United States Patent [19]

Adair

[11] Patent Number: 5,495,286
[45] Date of Patent: Feb. 27, 1996

[54] STERILE VIDEO MICROSCOPE HOLDER FOR OPERATING ROOM

[76] Inventor: Edwin L. Adair, 2800 S. University Blvd., Denver, Colo. 80210

[21] Appl. No.: 261,331

[22] Filed: Jun. 16, 1994

Related U.S. Application Data

[63] Continuation of Ser. No. 733,348, Jul. 22, 1991, abandoned.

[51] Int. Cl.⁶ .................................................. A61B 1/06
[52] U.S. Cl. .......................... 348/68; 348/77; 348/373; 600/109; 600/160
[58] Field of Search ........................... 358/93, 98, 108, 358/229; 348/61, 65, 66, 68, 71, 73, 75, 77, 373, 376; 128/4, 6; 354/81

[56] References Cited

U.S. PATENT DOCUMENTS

| | | | |
|---|---|---|---|
| 1,930,993 | 10/1933 | Blodgett . | |
| 2,290,793 | 7/1942 | Alderman . | |
| 3,417,746 | 12/1968 | Moore et al. . | |
| 3,891,842 | 6/1975 | Strusinski . | |
| 4,344,092 | 8/1982 | Miller | 348/77 |
| 4,573,452 | 3/1986 | Greenberg | 128/6 |
| 4,641,635 | 2/1987 | Yabe | 128/6 |
| 4,651,201 | 3/1987 | Schoolman | 358/98 |
| 4,802,460 | 2/1989 | Ohkuwa et al. | 128/6 |
| 4,867,404 | 9/1989 | Harrington et al. | 248/231.4 |
| 4,888,639 | 12/1989 | Yabe et al. | 128/6 |
| 4,914,521 | 4/1990 | Adair | 358/98 |
| 4,915,626 | 4/1990 | Lemmey | 348/77 |
| 4,961,110 | 10/1990 | Nakamura | 128/6 |
| 4,963,903 | 10/1990 | Cane | 354/81 |
| 5,007,408 | 4/1991 | Ieoka | 128/6 |
| 5,051,824 | 9/1991 | Nishigaki | 358/98 |
| 5,124,797 | 6/1992 | Williams | 358/93 |
| 5,184,601 | 2/1993 | Putman | 128/4 |
| 5,188,094 | 2/1993 | Adair | 128/6 |
| 5,224,680 | 7/1993 | Greenstein et al. | 248/316.4 |

*Primary Examiner*—Tommy P. Chin
*Assistant Examiner*—Bryan S. Tung
*Attorney, Agent, or Firm*—Fields, Lewis & Rost

[57] ABSTRACT

A sterilizable video microscope holder for supporting and positioning a video microscope unit in an operating room is provided which has a sterilizable flexible tubular arm, a bundle of optical fibers running through the arm, a support attached to one end of the arm for supporting it in the operating room and a connector at the same end of the arm for holding an end of the fiber optic bundle in aligned positioned for connection to a light source. The arm includes an inner articulated member which is bendable in all directions and will remain in any position to which it is bent and an outer covering over the inner articulated member to protect it from moisture, body oils and chemicals. The connector includes a tubular member for receiving and supporting the first end of the bundle of optical fibers in aligned position and an adaptor at a distal end of the tubular member connected to the first end of the bundle and being connectable to a light source.

17 Claims, 3 Drawing Sheets

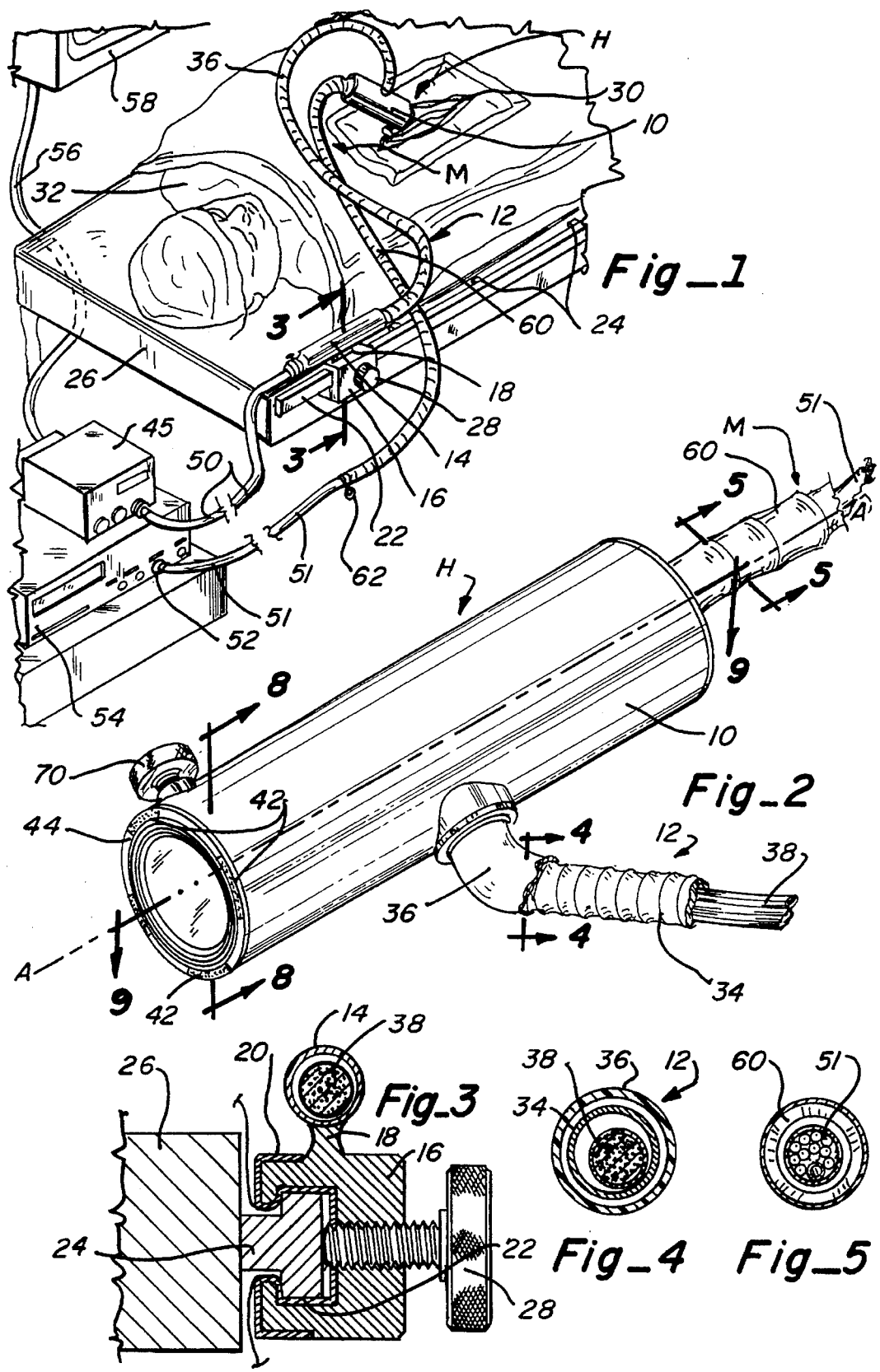

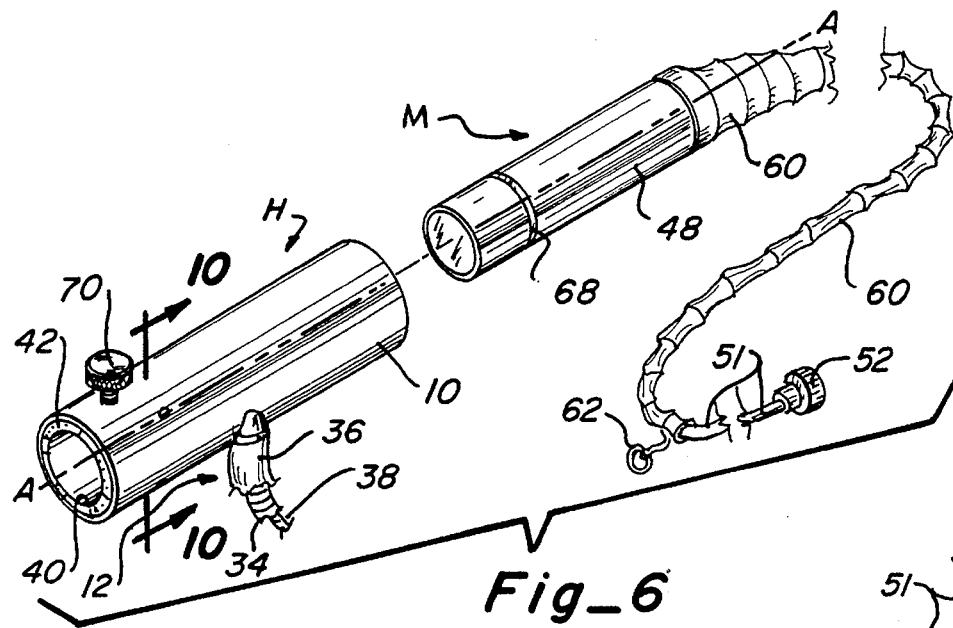
Fig_6
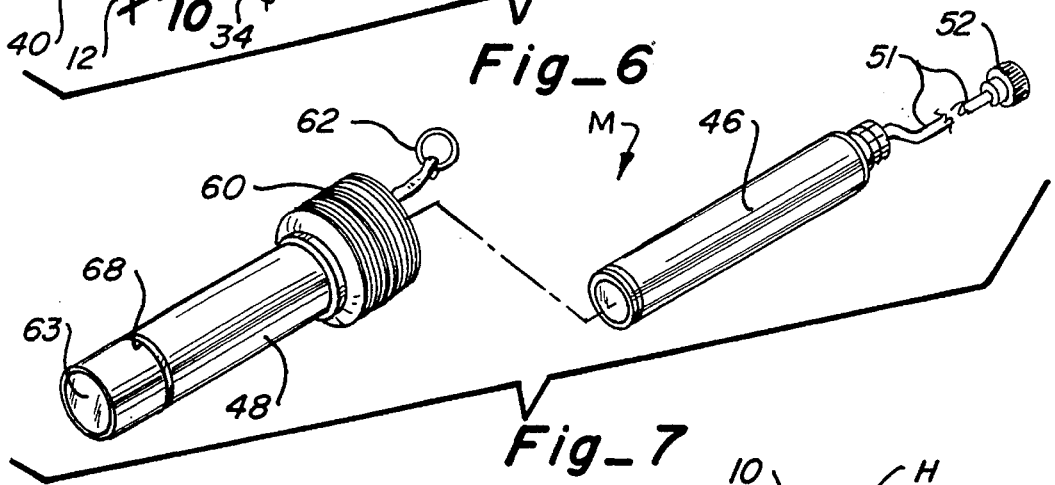
Fig_7
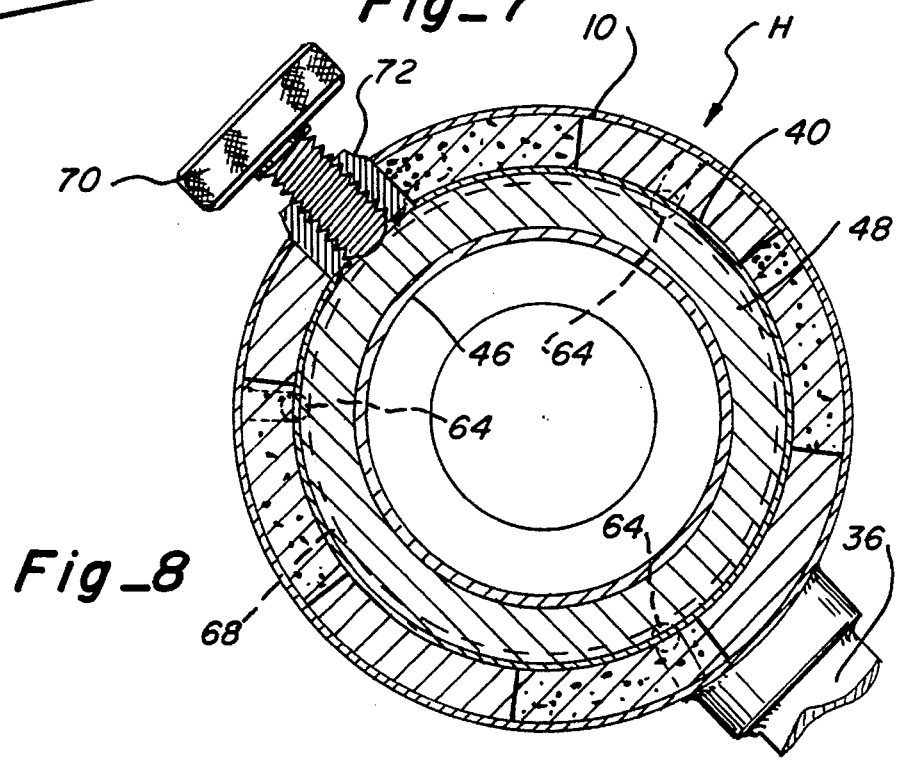
Fig_8

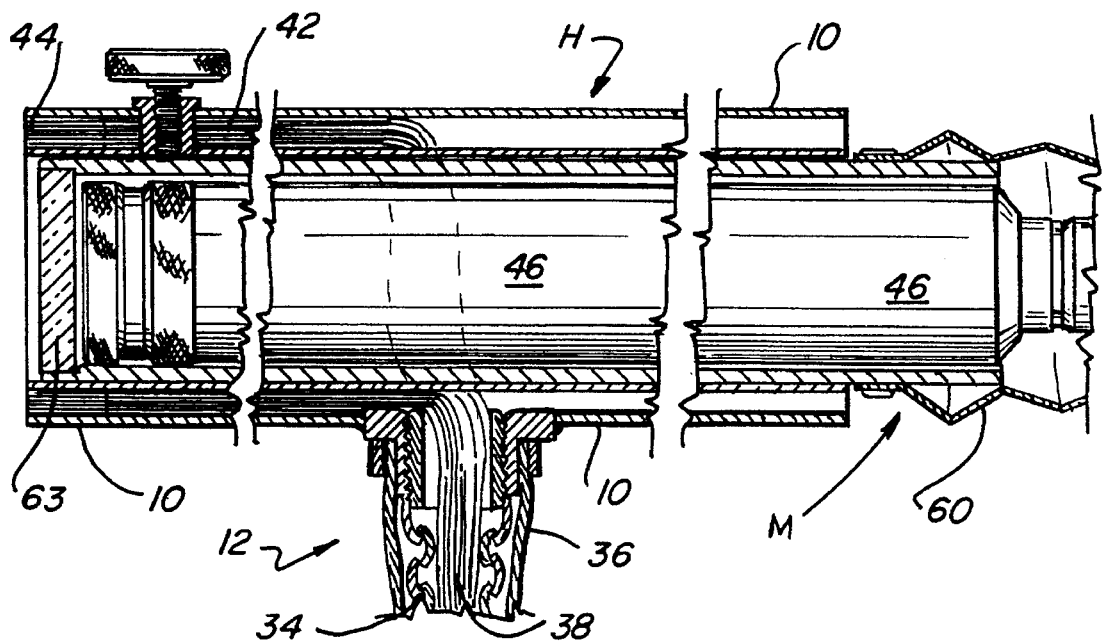
Fig_9
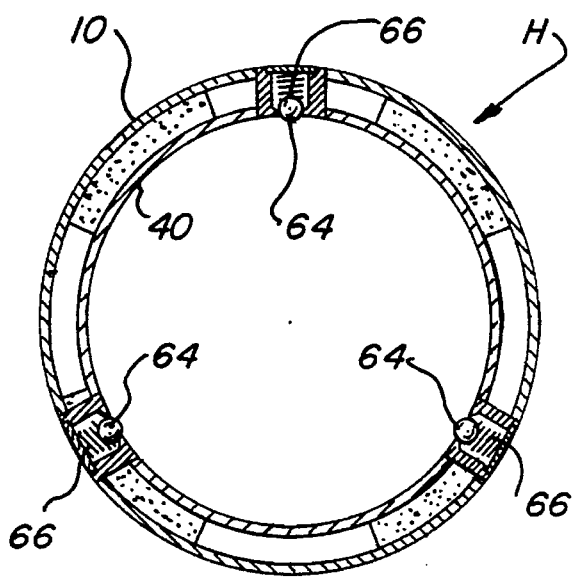
Fig_10

STERILE VIDEO MICROSCOPE HOLDER FOR OPERATING ROOM

This is a continuation of U.S. application Ser. No. 07/733,348 filed Jul. 22, 1991, now abandoned.

TECHNICAL FIELD

This invention relates to a sterile video microscope holder and more particularly to one for supporting a video microscope in the sterile field of the operating theater of an operating room and providing illumination to the site being viewed.

BACKGROUND ART

It is increasingly common to videotape operative procedures within the operating room. Typically, this is done by mounting a camera on an overhead surgical light or by mounting the camera on a headband worn by the surgeon. The surgical light with a camera mounted therein requires frequent adjustment, which is difficult since the light is not sterile. When the camera is mounted on a headband worn by the surgeon, it is difficult to watch the video since the surgeon's head is frequently in motion and the camera is directed all over the operating room rather than being focused solely on the operating site. The purpose of having a camera in the operating room in the past was for documentation and teaching purposes.

Much smaller sterile video cameras have been developed which heretofore were not available. However, prior to the present invention there was not a sterile mounting device for such cameras which could position them easily in the desired location within the sterile field for viewing the operating site under magnification and thereby provide the advantages and utility of an operating microscope or loupe.

U.S. Pat. No. 4,963,903 to Cane provides a magnifying camera which is supported on a gooseneck attached to a clamp outside the sterile field. This device is not sterile and therefore must be draped and disinfected by soaking. Also, it has no internal light source and therefore may cast a shadow over the operating site. It is intended for recording the operation and not to assist the surgeon during the operation.

My U.S. Pat. No. 4,914,521 for "Sterilizable Video Camera Cover" discloses a camera and camera cover for use in an operating room wherein each may be sterilized for use in this environment. However, no means is disclosed for supporting and holding the camera in a desired position during an operative procedure.

U.S. Pat. No. 3,891,842 to Strusinski for "Optical Device" discloses a device on the center of a light used in surgery which forms a handle for manipulating the position of the light and also serves as a holder for a television camera so that the camera can be aimed in the direction of the maximum intensity of the light. The light source is pivoted or gimboled so as to align it in any suitable position with respect to the patient.

U.S. Pat. No. 3,417,746 to Moore et al. for "Illuminating Endoscope With Disposable Elements" shows a fiber light source which is positioned around the periphery of an endoscope. However, it does not have any means for supporting it in a desired position within an operating room.

U.S. Pat. No. 1,930,993 to Blodgett for "Lamp Support" shows a lamp mounted on a flexible support for use over a dental chair.

U.S. Pat. No. 2,290,793 to Alderman for "Combination Camera and Illuminator" discloses a lighting device which supports a camera at the center thereof. However, the device and camera are hand held and are not mounted for use in an operating room.

DISCLOSURE OF THE INVENTION

In accordance with this invention, a sterile video microscope holder for supporting and positioning a video microscope unit in an operating room and in a sterile field for assisting the surgeon during the operation is provided which has a flexible tubular arm, a bundle of optical fibers running through the arm, means attached to one end of the arm for supporting the arm in the sterile field within the operating room, a connector at the same end of the arm for holding an end of the fiber optic bundle in aligned positioned for connection to a light source, a sleeve attached to the other end of the arm for receiving and supporting the camera unit and light transmitting means positioned within the sleeve and connected to the other end of the bundle of optical fibers. The arm includes an inner articulated member which is bendable in all directions and will remain in any position to which it is bent and an outer covering over the inner articulated member to protect it from moisture, body oils and chemicals. The connector includes a tubular member for receiving and supporting the first end of the bundle of optical fibers in aligned position and an adaptor at a distal end of the tubular member connected to the first end of the bundle and being connectable to a light source. These light fibers are made of a material which will not melt if the arm is placed in an autoclave for heat sterilization.

The mounting means may comprise a C-clamp slidably mounted on the support and locking means on the clamp for releasably locking the C-clamp to the support. A layer of low friction material, such as Teflon, can be provided on the surface of the C-clamp which comes in contact with the support to facilitate movement therealong to adjust the location of the arm. Also, the Teflon can withstand the high heat of sterilization. The sleeve can include an outer tube of a first diameter and an inner tube of lesser diameter concentrically mounted with light transmitting means mounted in the space between the inner and outer tubes. A longitudinal axis defines the tubular shape of the sleeve. A plurality of spring detents can be spaced around the sleeve and extend inwardly from the inner sleeve for releasable engagement with a circumferential groove around the video microscope unit so that the video microscope unit can be rotated within the sleeve for desired orientation of a highly magnified image on a T.V. monitor. In addition, means for locking the video microscope unit in an adjusted rotational position are provided. The video microscope unit can include a sterile cylindrical cover having an optically clear window at one end for receiving the video microscope and an accordion-folded side walls which can be extended over the video microscope and cables when the video microscope is placed in the sleeve in the operating room. In addition, the camera can provide magnification so that the image viewed on a video monitor is enlarged to assist the surgeon during the operation.

From the foregoing, it can be seen that a video microscope and video microscope holder have been provided in combination which are each sterilizable for use in an operating room environment and yet can be easily manipulated and positioned for viewing the site in the operating theater for the purpose of doing surgery under magnification, recording the event, for instruction and analysis following the operation. After the operation is completed, the video microscope and cover can be resterilized for use for another operation as can the holder. Since it is sterilized, it can be introduced inside a body cavity for viewing areas which are not possible to see with prior art devices. Thus, an economical apparatus has been provided for use in the operating room for viewing and recording the operative procedure, in ways not previously possible.

Additional advantages of the invention will become apparent from the description which follows, taken in conjunction with the accompanying drawings.

BRIEF DESCRIPTION OF THE DRAWINGS

FIG. 1 is a perspective view of a sterile video microscope supported by a video microscope holder within an operating room in accordance with this invention;

FIG. 2 is an enlarged view of the video microscope holder of FIG. 1;

FIG. 3 is an enlarged vertical section, taken along line 3—3 of FIG. 1, showing the clamp for attaching the video microscope holder on a rail at the side of an operating table;

FIG. 4 is an enlarged section, taken along line 4—4 of FIG. 2, showing the optical fibers coming into the video microscope holder;

FIG. 5 is a slightly enlarged section, taken along line 5—5 of FIG. 2, showing the cables and the cover for the video microscope;

FIG. 6 is an exploded view of the holder and the video microscope unit of this invention;

FIG. 7 is an exploded view of the video microscope and cover of FIG. 6;

FIG. 8 is a greatly enlarged vertical section, taken along line 8—8 of FIG. 2, showing further details of the holder and the means for locking the video microscope in fixed position;

FIG. 9 is an enlarged horizontal section, taken along line 9—9 of FIG. 2, showing further details of the video microscope holder and video microscope unit; and FIG. 10 is an enlarged vertical section, taken along line 10—10 of FIG. 6, showing the spring detent and groove arrangement for rotatably supporting the video microscope unit within the holder.

BEST MODE FOR CARRYING OUT THE INVENTION

According to this invention, a video microscope holder H is provided for receiving a video microscope unit M. As best viewed in FIG. 1, the video microscope holder H includes a sleeve 10 supported by a flexible arm 12. Sleeve 10 is tubular in shape and has a longitudal axis A—A. Conveniently, one end of arm 12 is connected to sleeve 10 and the other end is connected to a cylindrical connector 14. Connector 14 is attached to a support 16 through a neck 18, as best seen in FIG. 3. Support 16 is C-shaped in crosssection and has a liner 20 made of a material having a low coefficient of friction, such as Teflon, for sliding along a rail 22 attached by connectors 24 to the side of an operating table 26. The Teflon will also withstand the heat of sterilization within an autoclave. The support 16 can be held in adjusted position along rail 22 by means of set screw 28 threadably received in support 16, as shown. Thus, the video microscope unit M can be positioned as desired to view an operating site 30 on a patient 32 laying on table 26. The video microscope unit may have variable magnification and zoom capabilities. Since it is sterile it may be operated by the physician as required during an operative procedure.

As seen in FIGS. 2 and 4, flexible arm 12 includes a coiled hollow member 34, such as the material which forms the arm of a goose-neck lamp, which can be bent to any desired shape and will remain in whatever position it is placed. An outer jacket 36 in the form of a tubing extends over member 34 to prevent moisture and greases from entering the tubing and adversely affecting the holding power of the joints of the adjustable arm. Conveniently, this jacket may be made of Teflon to withstand heat sterilization. A optical fiber bundle 38 extends through the hollow center of flexible arm 12. This bundle is made of a material which will withstand heat sterilization. The distal end of this bundle 38 is separated within holder H and is spaced around holder H between the outer sleeve 10 and an inner sleeve 40, such as in four grouped segments 42, as best seen in FIG. 2. The ends of these segments are positioned behind a lens 44 at the distal end of housing H between inner and outer sleeves 10 and 40, respectively.

A light source 45 is provided which is connected by means of a light cable 50 to cylindrical connector 14 for aligning cable 50 with the optical fiber bundle 38. The light is focused by lens 44 on the operating site 30. The light source 45 can provide any selected light frequency or can be provided with filters to selectively provide the appropriate light frequencies for the procedure involved.

The video microscope unit M comprises a video microscope 46 received in a sterilizable sheath 48. The video microscope has a cable 51 which houses appropriate wiring for transmitting a signal from the video microscope to a connector 52 which can be attached to a VCR 54. A signal can be provided from the VCR through a cable 56 to a T.V. monitor 58 for viewing the image the video microscope takes of the operating site 30. This image can be magnified up to 200 times or more. Thus, the physician can view the monitor during the operation and use it instead of a conventional operating microscope of loupe to perform the operative procedure. The sheath 48 is provided with sleeve 60 having accordion pleats so that the sleeve can be pulled by means of a tab 62 along cable 50 to provide a sterile covering for the video microscope. This apparatus is described in my U.S. Pat. No. 4,914,521 for "Sterilizable Video Camera Cover", the subject matter thereof being incorporated herein by reference. As shown in that patent, means are provided for releasably locking the camera, i.e., the video microscope 46 within sheath 48 so that there is no relative movement between the two during use. When a video microscope is placed in the sheath, the forward end thereof is placed in proximity to an optically clear window 63 at the forward end of sheath 48.

As best seen in FIG. 10, housing H is provided with a plurality of ball detents 64 which are urged inwardly by springs 66, as shown. As shown in FIG. 8, these ball detents are engagable in a circumferential groove 68 in sheath 48 when the video microscope unit is placed in the housing. The groove and ball detents hold the video microscope unit in releasable fixed position within the housing and allow the video microscope to be rotated within the housing to properly orient the image on the monitor 58. Once the proper orientation is achieved, the video microscope unit can be held in place by thumb screw 70 which extends through a threaded collar 72, of housing H, as seen in FIG. 8. Thus, the present apparatus can serve as an operating microscope for replacement of the standard optical loupe.

Advantageously, the video microscope can have an automatic focus and automatic iris and zoom capabilities for magnification up to two hundred times or more. In addition to recording events in an operating room, the surgeon can look at the monitor 58 to see a magnified surgical field to assist him in the optical procedure. Also, the video microscope unit and video microscope holder can be of sufficiently small size as to be introduced into the chest cavity, abdominal cavity or other areas which previously have been inaccessible sites for viewing. Thus, the present invention has major use in surgical microscopy in the operating room. While the video microscope holder has been shown on a rail on the operating table, it could be mounted on a I.V. stand or on a self-retaining retractor positioned around the incision at the operating site. Also, by using the holder in combination with a video microscope having a sterile sheath and cover over it, can be used within the operating theater without compromising the sterility thereof. Also, since the video microscope and holder are sterile they can be adjusted or moved by the physician during the surgical procedure without compromising the sterility of the operating room.

I claim:

1. A sterilizable holder for supporting and positioning a non-illuminating video camera having a distal end for viewing a desired surgical area in a sterile operating field of an operating room and providing illumination to the desired surgical area, said sterilizable holder comprising:

a flexible, heat sterilizable, tubular arm having first and second ends;

at least one heat sterilizable optical fiber running through said arm, said at least one having first and second ends;

means attached to said first end of said arm for supporting said arm in the sterile operating field of the operating room;

a connector at said first end of said arm holding said first end of said at least one fiber in aligned position for connection to a light source;

a tubular holder, having a longitudinal axis, a first proximal end through which the non-illuminating video camera extends and having a second distal end at which the distal end of the non-illuminating video camera is positionable for viewing the surgical area along said axis, said tubular holder attached to said second end of said arm for removably receiving and supporting the non-illuminating video camera, said tubular holder further including an outer sleeve having a first diameter and an inner sleeve having a second diameter, said inner sleeve concentrically mounted within said outer sleeve;

adjustable means mounted on said tubular holder for selectively positioning the distal end of the non-illuminating video camera adjacent said distal end of said tubular holder; and said second end of said at least one optical fiber extending between said inner and outer sleeves of said tubular holder, said second end of said optical fiber having a distal tip positioned near said distal end of said tubular holder for providing circumferential illumination to the desired surgical area.

2. Apparatus, as claimed in claim 1, wherein said at least one heat sterilizable optical fiber is positionable equidistantly around said second diameter of said inner sleeve.

3. Apparatus, as claimed in claim 1, wherein said arm comprises:

an inner articulated member which is bendable in all directions and will remain in any position to which said member is bent; and an outer heat sterilizable covering positionable over said inner articulated member to protect said member from moisture, body oils and chemicals.

4. Apparatus, as claimed in claim 1, wherein said connector comprises:

a means for receiving and supporting said first end of said at least one optical fiber in said aligned position, said means for receiving and supporting having proximal and distal ends; and an adaptor locatable at said distal end of said means for receiving and supporting and connected to said first end of said at least one fiber for connection to said light source.

5. Apparatus, as claimed in claim 1, wherein said tubular holder further includes:

a window means sealed at a distal end of said tubular holder for providing a transparent surface enabling light to be received by said non-illuminating video camera.

6. Apparatus, as claimed in claim 5, further including:

a plurality of spring detents positioned around said tubular holder and extending radially inward from said inner sleeve for releasable engagement with the non-illuminating video camera so that the video camera can be rotated within said inner sleeve for the desired orientation of an image to be observed on a visual monitor.

7. Apparatus, as claimed in claim 6, further including:

a locking device mounted on said tubular holder for locking said video camera in the desired orientation.

8. Apparatus, as claimed in claim 22, further including:

a window means at said distal end of said tubular holder for providing a transparent surface enabling light to be received by said non-illuminating video device;

a plurality of spring detents positioned around said tubular holder in a common transverse plane and extending radially inward from said inner sleeve for releasable engagement with a mating surface of the non-illuminating video device so that the non-illuminating video device can be rotated within said inner sleeve for the desired orientation of an image to be observed on a visual monitor; and a locking device mounted on said tubular holder for locking said video device in the desired orientation.

9. Apparatus, as claimed in claim 8, wherein said at least one segment is positionable equidistantly around said second diameter of said inner sleeve.

10. Apparatus, as claimed in claim 8, wherein said arm comprises:

an inner articulated member which is bendable in all directions and will remain in any position to which said member is bent; and an outer heat sterilizable covering over said inner articulated member to protect said member from moisture, body oils and chemicals.

11. Apparatus, as claimed in claim 8, wherein said connector comprise:

a means for receiving and supporting said first end of said at least one optical fiber in said aligned position; and an adaptor at a distal end of said means for receiving and supporting connected to said first end of said at least one fiber and being connectable to said light source.

12. Apparatus, as claimed in claim 1, wherein:

said at least one optical fiber comprises a plurality of optical fibers arranged in a plurality of grouped segments between said inner and outer sleeves of said tubular holder.

13. A sterilizable illuminated holding device for illuminating a desired surgical area and for positioning a distal end of a non-illuminating video camera for viewing the illuminated surgical area, said device comprising:

a tubular holder having concentric inner and outer sleeves forming an annular space therebetween and mounted about a longitudinal axis of said holder, said holder having a distal end through which the video camera can view the surgical area and a proximal end for insertion of the video camera into said holder along said longitudinal axis;

adjustable means mounted to said inner sleeve for selectively positioning the distal end of the video camera adjacent said distal end of said tubular holder;

adjustable support means attached to said tubular holder for supporting said holder in a suitable adjusted position for the holder to illuminate the surgical area and for the video camera to view the illuminated surgical area; and a plurality of optical fibers positioned within and around said annular space, said plurality of optical fibers each having a first distal tip positioned at said distal end of said tubular holder for projecting light to the surgical area, and having a second proximal end connectable to a source of illumination.

14. Apparatus, as claimed in claim 13, wherein said adjustable support means includes:

a flexible, tubular arm having a first end connected to said outer sleeve and having a second end, said plurality of optical fibers extending through said tubular arm and into said annular space;

means attached to said second end of said tubular arm for supporting said arm and said housing in the sterile operating field of the operating room.

15. Apparatus, as claimed in claim 13, wherein:

said first distal tip of each of said optical fibers is spaced around said longitudinal axis of said tubular holder.

16. Apparatus, as claimed in claim 15, wherein:

said first distal tip of each of said optical fibers is arranged in groups as spaced segments around said annular space at said distal end of said holder.

17. A sterilizable illuminated holding device for illuminating a desired surgical area and for positioning a distal end of a non-illuminating video camera for viewing the illuminated surgical area, said device comprising:

a tubular holder having concentric inner and outer sleeves forming an annular space therebetween and mounted about a longitudinal axis of said holder, said holder having a first distal end through which the video camera can view the surgical area and a second proximal end for insertion of the video camera into said holder along said longitudinal axis;

adjustable means mounted to said inner sleeve for selectively positioning the distal end of the video camera adjacent said distal end of said tubular holder;

a flexible, tubular arm attached to said holder for supporting said holder in a suitable adjusted position for the holder to illuminate the surgical area and for the video camera to view the illuminated surgical area, said arm having a first end connected to said outer sleeve and having a second end;

means attached to said second end of said tubular arm for supporting said arm and said holder in the sterile operating field of an operating room; and a plurality of optical fibers extending through said tubular arm and into said annular space, said plurality of optical fibers each having a first distal tip positioned at said distal end of said holder for projecting light to the surgical area, said first distal tip of each of said plurality of optical fibers being arranged in groups as spaced segments around said annular space at said distal end of said holder, and said plurality of optical fibers each having a second end connectable to a source of illumination.

* * * * *

UNITED STATES PATENT AND TRADEMARK OFFICE
CERTIFICATE OF CORRECTION

PATENT NO. : 5,495,286

DATED : February 27, 1996

INVENTOR(S) : Edwin L. Adair

It is certified that error appears in the above-identified patent and that said Letters Patent is hereby corrected as shown below:

```
Column 2, line 54, delete "an";
Column 6, line 34, delete "22" and insert --1--;
          line 38, delete "device" and insert --camera--;
          line 43, delete "device" and insert --camera--;
          line 44, delete "device" and insert --camera--; and
          line 48, delete "device" and insert --camera--.
```

Signed and Sealed this

Seventh Day of April, 1998

Attest:

BRUCE LEHMAN

Attesting Officer      Commissioner of Patents and Trademarks